(12) United States Patent
Little et al.

(10) Patent No.: US 6,747,784 B2
(45) Date of Patent: Jun. 8, 2004

(54) COMPLIANT MECHANISM AND METHOD OF FORMING SAME

(75) Inventors: Michael Little, Oak Park, CA (US); Thomas S. Tyrie, Oak Park, CA (US); William P. Eaton, Thousand Oaks, CA (US)

(73) Assignee: NP Photonics, Inc., Tucson, AZ (US)

( * ) Notice: Subject to any disclaimer, the term of this patent is extended or adjusted under 35 U.S.C. 154(b) by 0 days.

(21) Appl. No.: 10/126,972

(22) Filed: Apr. 22, 2002

(65) Prior Publication Data

US 2002/0196522 A1 Dec. 26, 2002

Related U.S. Application Data

(63) Continuation-in-part of application No. 10/085,143, filed on Mar. 1, 2002, now Pat. No. 6,665,109, which is a continuation-in-part of application No. 09/811,612, filed on Mar. 20, 2001, now Pat. No. 6,519,074, which is a continuation-in-part of application No. 09/766,687, filed on Jan. 19, 2001, now Pat. No. 6,597,461, said application No. 10/085,143, filed on Mar. 3, 2001

(60) Provisional application No. 60/211,529, filed on Jun. 15, 2000, provisional application No. 60/190,111, filed on Mar. 20, 2000, provisional application No. 60/284,943, filed on Apr. 20, 2001, and provisional application No. 60/303,772, filed on Jul. 10, 2001.

(51) Int. Cl.[7] .................... G02B 26/00; G02B 26/08; G02B 7/02
(52) U.S. Cl. .................... 359/290; 359/291; 359/295; 359/298; 359/224; 359/814
(58) Field of Search ..................... 359/214, 224, 359/290, 291, 298, 811, 813, 814, 824, 198, 292; 257/254; 356/454; 310/36

(56) References Cited

U.S. PATENT DOCUMENTS 3,978,508 A * 8/1976 Vilkomerson ............ 257/254

(List continued on next page.)

FOREIGN PATENT DOCUMENTS

| EP | 0 702 205 A2 | 8/1995 |
| WO | WO 99/34484 | 7/1999 |

OTHER PUBLICATIONS

Joost C. Lotters et al.; "Polydimethylisiloxane as an elastic material applied in a capacitive accelerometer"; (1996); J. Micromech. Microeng. 6 (1996) pp. 52–54.

P. Bley; "Polymers–an Excellent and Increasingly Used Material for Microsystems"; Sep. 1999; SPIe vol. 3876; pp. 172–184.

Thorbjorn Ebeforst et al.; "New small radius joints based on thermal shrinkage of polyimide in V–grooves for robust self–assembly 3D microstructures"; J. Micromech. Microeng. 8 (1998); pp. 188–194.

M Pedersent et al.; "A capacitive differential pressure sensor with polyimide diaphragm"; J. Micromech. Microeng. 7 (1997); pp. 250–252.

(List continued on next page.)

*Primary Examiner*—Georgia Epps
*Assistant Examiner*—Jack Dinh
(74) *Attorney, Agent, or Firm*—Fleshner & Kim LLP

(57) ABSTRACT

The present invention provides a compliant mechanism that can be used to make a variety of devices, such as tunable optical devices, that are more reliable, more cost effective, and/or exhibit better performance than prior art devices. In one embodiment, the complaint mechanism includes an island that is suspended from a frame using a compliant member that is attached to the frame and the island. Individual actuators and/or sensor elements may be placed on the island, so that each island may be individually actuated or sensed.

23 Claims, 6 Drawing Sheets

U.S. PATENT DOCUMENTS

| | | | | |
|---|---|---|---|---|
| 4,203,128 A | | 5/1980 | Guckel et al. | 357/60 |
| 4,400,058 A | | 8/1983 | Durand et al. | 350/166 |
| 4,553,816 A | | 11/1985 | Durand et al. | 350/166 |
| 4,566,935 A | | 1/1986 | Hornbeck | 156/626 |
| 4,825,262 A | | 4/1989 | Mallinson | 356/352 |
| 4,859,060 A | * | 8/1989 | Katagiri et al. | 356/454 |
| 5,068,861 A | | 11/1991 | Abbott et al. | 372/20 |
| 5,313,333 A | | 5/1994 | O'Brien et al. | 352/820 |
| 5,381,232 A | | 1/1995 | Van Wijk | 356/352 |
| 5,383,168 A | | 1/1995 | O'Brien et al. | 369/44.14 |
| 5,461,507 A | | 10/1995 | Westland et al. | 359/289 |
| 5,510,914 A | | 4/1996 | Liu et al. | 359/56 |
| 5,561,523 A | * | 10/1996 | Blomberg et al. | 356/454 |
| 5,822,110 A | | 10/1998 | Dabbaj | 359/293 |
| 5,917,647 A | | 6/1999 | Yoon | 359/298 |
| 5,931,925 A | | 8/1999 | McNabb et al. | 710/52 |
| 5,970,190 A | | 10/1999 | Fu et al. | 385/37 |
| 5,987,479 A | | 11/1999 | Oliver | 707/205 |
| 6,049,407 A | * | 4/2000 | Melville | 359/198 |
| 6,078,395 A | | 6/2000 | Jourdain et al. | 356/352 |
| 6,137,819 A | | 10/2000 | Najda | 372/96 |
| 6,175,443 B1 | * | 1/2001 | Aksyuk et al. | 359/291 |
| 6,198,180 B1 | * | 3/2001 | Garcia | 310/36 |
| 6,263,371 B1 | | 7/2001 | Geagan, III et al. | 709/231 |
| 6,324,192 B1 | | 11/2001 | Tayebati | 372/20 |
| 6,335,817 B1 | | 1/2002 | Phillipps | 359/290 |
| 6,400,738 B1 | | 6/2002 | Tucker et al. | 372/20 |
| 6,433,917 B1 | * | 8/2002 | Mei et al. | 359/292 |

OTHER PUBLICATIONS

Frank Niklaus et al.; "Low–temperature full wafer adhesive bonding"; J. Micromech. Microeng. 11 (2001); pp. 100–107.

Kenji Suzuki et al.; "Insect–Model Based Microrobot with Elastic Hinges"; Journal of Microelectromechanical Systems, vol. 3, No. 1, Mar. 1994; pp. 4–9.

K. Minami et al.; "Fabrication of Distributed Electrostatic Electrostatic Micro Actuator (DEMA)"; Journal of Microelectromechanical Systems, vol. 2, No. 3, Sep. 1993; pp. 121–127.

Cheol–Hyun Han et al.; "Parylene–Diaphragm Piezoelectric Acoustic Transducers"; The Thirteenth Annual International Conference on Microelectromechanical Systems; (2000), pp. 148–152.

Krzysztof A R B Pietraszewski et al.; "Cryogenic servo–stabilised Fabry–Perot Interferometer for imaging at 2–2.5microns"; SPIE Proceedings, vol. 2814 (1996); pp. 139–146.

T R Hicks et al.; "The application of capacitance micrometry to the control of Fabry–Perot etalons"; J. Phys. E. Instrum., vol. 17, 1984, pp. 49–55.

P. Tayebati et al.; "Widely Tunable Fabry–Perot filter Using Ga(Al)As–AlO$_x$ Deformable Mirrors"; IEEE Photonics Technology Letters, vol. 10, No. 3, Mar. 1998; pp. 394–396.

P. Tayebati et al.; "Microelectromechanical tunable filters with 0.47nm linewidth and 70nm tuning range"; Electonics Letters; Jan. 8, 1998; vol. 34, No. 1; pp. 76–78.

M. C. Larson et al.; "Vertical Coupled–Cavity Microinterferometer on GaAs with Deformable–Membrane Top Mirror"; IEEE Photonics Technology Letters, vol. 7, No. 4, Apr. 1995; pp. 382–384.

K. Aratani et al.; "Process and Design Considerations for Surface Micromachined Beams for a Tunable Interferometer Array in Silicon"; Proc. IEEE Micro Electro Mechanical Systems, Ft. Lauderdal, FL, 1993, pp. 230–235.

MEM–TUNE Tunable Filter; Preliminary Data Sheet; May 2000.

OPM–1 Optical Performance Monitor; Preliminary Data Sheet; May 2000.

GTM–1 EDFA Gain–Tilt Monitor; Preliminary Data Sheet; May 2000.

J. H. Jerman et al.; "Miniature Fabry–Perot Interferometers Micromachined in Silicon for use in Optical Fiber WDM Systems"; Transducers'91, International Solid–State Conference on Sensors and Actuators, pp. 372–375 (1991) IEEE, pp. 472–475.

P. Tayebati; "Microelectromechanical tunable filter with stable haft synmetric cavity"; Electronics Letters–IEEE, 1998, p. 1967.

E. Ollier et al.; "Micro–Opto–Electro–Mechanical Systems: Recent developments and LETI's acitivities"; SPIE: vol. 4075; pp. 12–21, Aug. 2000.

T. R. Hicks et al.; "The application of capacitance micrometry to the control of Fabry–Perot etalons"; J. Phys. E: Sci. Instrum., vol. 17, 1984; pp. 49–55.

A Reference Model for Streaming Media Management. NaviSite, Inc., 1–11 (Dec. 2000).

Wu, D. et al. Streaming Video over the Internet: Approaches and Directions. *IEEE Transactions on Circuits and Systems for Video Technology* 11 282–300 (Mar. 2001).

* cited by examiner

COMPLIANT MECHANISM AND METHOD OF FORMING SAME

RELATED APPLICATIONS

This application claims priority to U.S. Provisional Application No. 60/284,943, filed Apr. 20, 2001. This application is also a continuation-in-part of U.S. patent application Ser. No. 10/085,143 filed Mar. 1, 2002 now U.S. Pat. No. 6,665,109 entitled "Compliant Mechanism and Method of Forming Same," which is a continuation-in-part of U.S. patent application Ser. No. 09/811,612 filed Mar. 20, 2001 now U.S. Pat. No. 6,519,074, entitled "Electrostatically-Actuated Tunable Optical Components Using Entropic Materials", which is a continuation-in-part of U.S. patent application Ser. No. 09/766,687 filed Jan. 19, 2001 now U.S. Pat. No. 6,597,461, entitled "Tunable Fabry-Perot Interferometer Using Entropic Materials." U.S. patent application Ser. No. 09/811,612 also claims priority to U.S. Provisional Application No. 60/190,111, filed Mar. 20, 2000 and No. 60/211,529, filed Jun. 15, 2000. U.S. patent application Ser. No. 10/085,143 also claims priority to U.S. Provisional Application No. 60/284,943, filed Apr. 20, 2001 and No. 60/303,772, filed Jul. 10, 2001. All of the above applications are hereby incorporated by reference in there entirety.

BACKGROUND OF THE INVENTION

1. Field of the Invention

This invention relates to a mechanism that can be used to make a variety of devices where precise positioning of a device element is desirable. Examples include tunable optical elements such as mirrors, lenses, filters, prisms and diffraction gratings for use in tunable optical devices.

2. Background of the Related Art

There is a continuing need for precise positioning of optical elements in devices for various applications, such as optical systems including imaging systems and telecommunications networks. Such precise positioning offers benefits such as tunable devices and simplified packaging.

Existing technologies for precise positioning of optical elements are either to costly, unreliable, or do not exhibit the performance needed for present and/or future systems requirements.

SUMMARY OF THE INVENTION

An object of the invention is to solve at least the above problems and/or disadvantages and to provide at least the advantages described hereinafter.

The present invention provides a compliant mechanism that can be used to make a variety of devices that are more reliable, more cost effective and/or exhibit better performance than prior art devices. The present invention further provides an actuated compliant mechanism for precisely positioning optical elements in optical devices.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Preferred embodiments of the invention will be described in detail with reference to the following drawings in which like reference numerals refer to like elements wherein.

DETAILED DESCRIPTION OF PREFERRED EMBODIMENTS

Figure 1:
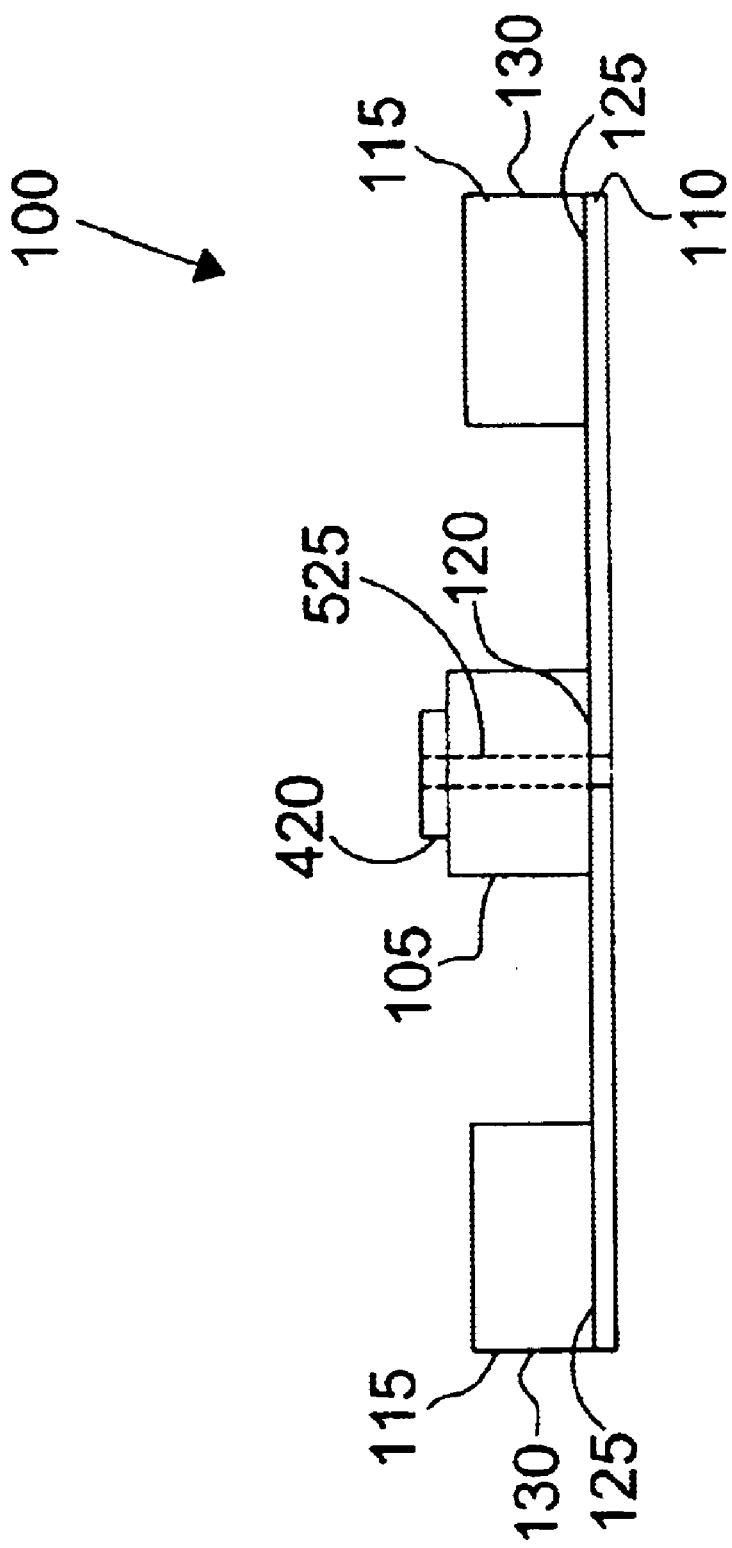
FIG. 1 is a cross-sectional view of a compliant mechanism, in accordance with an embodiment of the present invention.

FIG. 1 shows one embodiment of the compliant mechanism 100 of the present invention. The compliant mechanism 100 includes an island 105, which is suspended from a frame 115 using a compliant member 110, which is attached to the frame 115 and the island 105. The junction or interface where the island 105 meets the compliant member 110 is the first interface 120. The junction or interface where the compliant member 110 meets the frame 115 is the second interface 125. The exterior surface of the frame 115 includes an outer frame edge 130.

The island 105 is preferably formed from a material that is more rigid than the compliant member 110, and preferably has a higher Young's modulus than the compliant member 110. Examples of such materials include polymers and other organic materials. The compliant member 110 is preferably an elastic material, preferably a polymer with a Young's modulus smaller than the Young's modulus of the island 105 and frame 115, and preferably has a relatively high elastic limit. In one preferred embodiment, the Young's modulus of the compliant member 110 is preferably less than 1 G Pascal. In embodiments where it is desirable to maintain the rigidity of the island 105 while the compliant member 110 is deformed, it is preferred that the Young's modulus of the island 105 is at least two orders of magnitude larger than the Young's modulus of the compliant member 110. Materials such as elastomers can offer Young's modulus as much as five orders of magnitude less than the Young's modulus of a typical silicon substrate. The frame 115 is preferably formed from a rigid material, which may be the same material used for the island 105.

To have the capability to achieve large motion or displacements, the compliant member 110 should preferably display linear-elastic behavior over a wide range of frequencies and over a substantial portion of the deformation range at low actuation forces. Entropic materials, such as elastomers, aerogels and other long-chained polymers, are one type of material which provides such behavior.

The term "island" is used for convenience in describing the invention and the preferred embodiments herein. The term does not imply isolation or separation from all elements of a device. Instead, it describes an element that is sufficiently separated from a support structure, such as the frame 115, so that the element can move relative to such support structure. The element may be movably or rigidly attached to one or more other elements in a device in certain embodiments.

An advantageous feature of certain embodiments of the invention is that the island is capable of having individual actuators and/or sensor elements placed on the island, so that each island may be individually actuated or sensed. Providing one or more rigid, discretely controlled islands with multiple actuators and/or sensors on each island allows for precision movement and/or sensing of each island. Such embodiments are advantageous for use with optical elements, but also can be used in other applications where precession movement and/or sensing is needed.

In general, the island 105 is formed of a first material, the compliant member 110 is formed of a second material and the frame 115 is formed of a third material. The first, second, and third materials may be the same, similar, or different materials or any combination thereof. It should be noted, however, that one preferred embodiment includes forming the island 105 and the frame 115 from a single wafer of etchable material causing the island 105 and the frame 115 to consist of the same material.

The island 105 has what is generally referred to as a "neutral position" which is the position the island 105 tends towards when not subjected to external forces. Thus, the island 105 tends to remain in a neutral position until an external force is applied to the island 105 which displaces the island 105 from the neutral position.

An optical component 420 may be supported by the island 105 of the compliant mechanism 100. The optical component 420 can include any variety of optical components or elements such as a fully reflective mirror, a partially reflective mirror, a hologram, a diffraction grating, a lens, prism, filter, various waveplates, etc. Note that other components requiring precise positioning can also be placed on the island 105 in substitution for, or in addition to the optical component 420.

The components of the compliant mechanism can be formed from a variety of materials. As described above, the island 105 is formed of a first material, which can be opaque, translucent, or transparent to electromagnetic radiation. The first material may also be an electrical conductor or an electrical insulator. Furthermore, the first material may be rigid or flexible. The optical component 420 may be intrinsic with the island 105 or affixed to the island 105 by any of various means well known in the art, such as bonding by various adhesives, or metallic bonding such as soldering, etc. The optical component 420 may also be formed using standard silicon or glass fabrication/processing techniques.

An aperture 525 (shown by dashed lines) may optionally extend through the optical component 420, the island 105 and the compliant member 110. The aperture 525 may have any symmetric or asymmetric shape. Alternatively, in lieu of forming an aperture 525 through the island 105 and the optical component 420, the island 105 may be formed from a material that is transparent to the wavelength of the light that will be impinging on the island 105 to allow light to pass through the island as desired.

Figure 2:
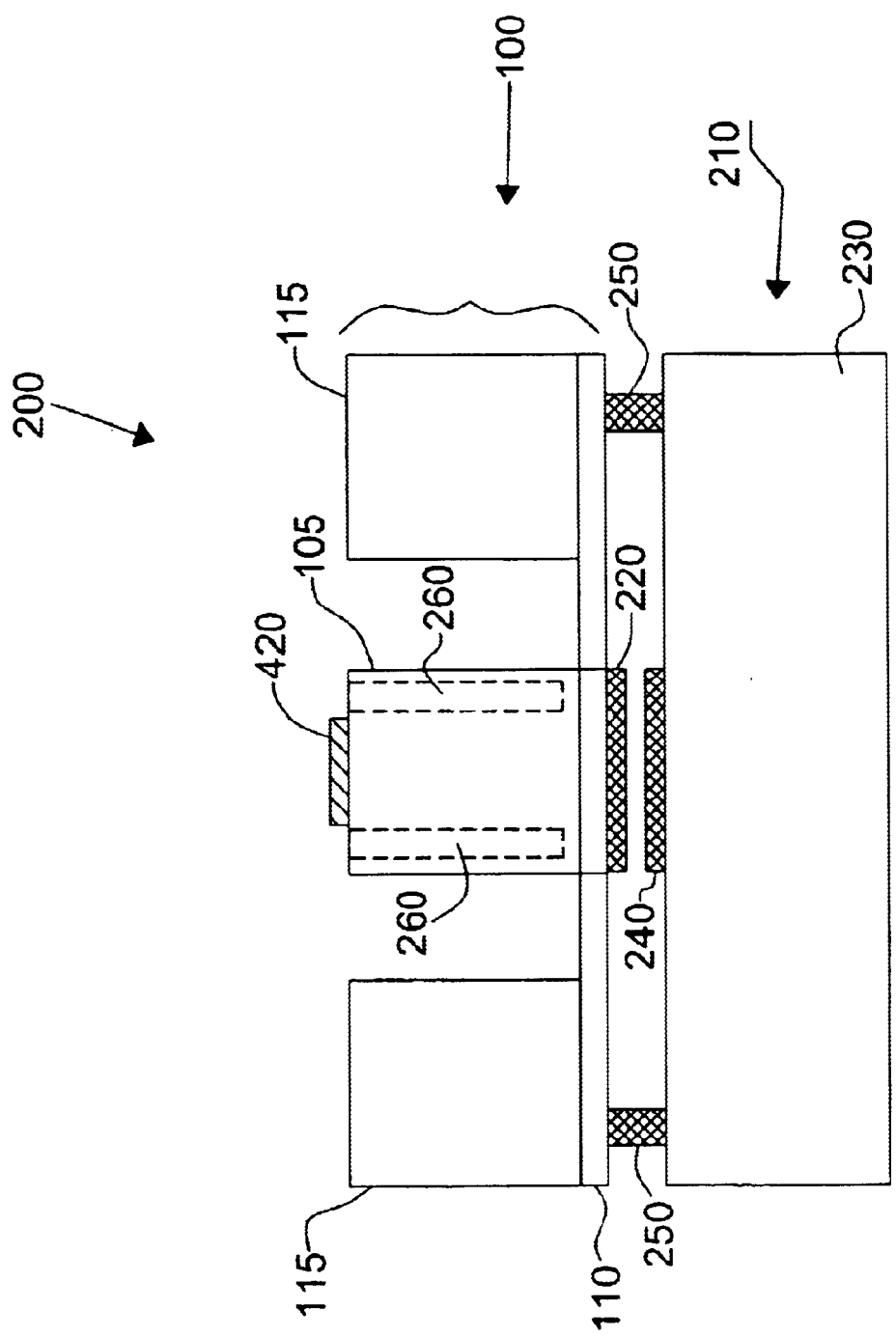
FIG. 2 is a cross-sectional view of an actuated device utilizing the compliant mechanism of FIG. 1, in accordance with one embodiment of the present invention.

FIG. 2 is a cross-sectional view of an actuated device 200, in accordance with one embodiment of the present invention. The actuated device 200 includes a compliant mechanism 100, which is disposed adjacent to an actuator support 210. The compliant mechanism 100 includes an island 105, which is attached to and supported by a compliant member 110. The compliant member 110 is also attached to a frame 115. Attached to the compliant member 110, underneath the island 105, is a first actuator 220. The first actuator 220 can include any number and configuration of magnetic, electrostatic, or mechanical force transducers, but are preferably electrodes configured for electrostatic actuation.

In the embodiment shown, the compliant member 110 has a prescribed thickness. The compliant member 110, however, could have any thickness. For example, it could have a thickness approximately equal to a width of the trench. The thickness of the compliant member 110 is preferably used to maintain the longitudinal stiffness. For example, as the thickness of the compliant member 110 is increased, there is increased longitudinal stiffness due to the properties of shear deformation. Thus, the compliant member 110 behaves more in shear mode as it becomes thicker.

In the embodiment shown, an optical component 420 is supported by the island 105. The optical component 420 can be a mirror, grating, or any other type of optical component. For example, the optical component 420 can be a dielectric stack mirror deposited onto the top surface of the island 105. The optical component 420 can also be formed intrinsically with the island 105.

The actuator support 210 includes an actuator frame 230 onto which is attached a second actuator 240. The second actuator 240 can include any configuration of force transducers which cooperatively function with the first actuator 220, but are preferably electrodes for electrostatic actuation. The compliant mechanism 100 is attached to the actuator support 210 by spacers 250. The spacers 250 serve to maintain a predetermined spacing between the second actuator 240 and the first actuator 220 when the actuators are not actuated.

In operation, the first and second actuators 220 and 240 can be controlled to apply a force to the island 105, thereby moving the island 105. The compliant member 110 exerts a restoring force to the island 105, which tends to urge the island 105 back into alignment with the frame 115 when the actuating force is removed.

In a preferred embodiment, the first and second actuators 220 and 240 comprise electrodes that are configured to generate an electrostatic force when a command signal is applied to the first and second actuators 220 and 240. The command signal applied to the first and second actuators 220 and 240 can be configured to create a repulsive or an attractive electrostatic force between the first and second actuators 220 and 240.

A feature of certain embodiments the present invention is that the actuation mechanism, comprised of the first and second actuators 220 and 240 in the embodiment of FIG. 2, is on a side of the compliant mechanism 100 opposite the optical component 420. This effectively separates the "drive cavity", which is the area between the compliant mechanism 100 and the actuator support 210, from any optical cavity that may be formed with the optical component 420. For example, the optical component 420 may be a mirror, and a second mirror may be positioned in a parallel relationship with optical component 420 to form a resonant optical cavity. The design of the actuated device 200 allows for independent optimization of the actuation mechanism and/or the optical cavity.

The island 105 represents a suspended mass, and the compliant member 110 represents a spring supporting the mass represented by the island 105. Thus, the island 105 and compliant member 110 combination is a mechanically resonant structure.

The mass of the island 105 and/or the spring constant of the compliant member 110 can be adjusted to obtain a predetermined resonant frequency. This can be useful if, for example, one wants to avoid movement of the island when the entire actuated device is physically moved at relatively low frequencies.

One way to adjust the resonant frequency of the island 105 and compliant member 110 combination is to adjust the mass of the island 105. However, there may be a limit as to how small the island 105 can be made because of the physical size of the optical component 420 that is supported by the island 105. As shown in FIG. 2, one way of removing mass from the island 105 is to create voids 260 (represented by dashed lines) in the island 105 by etching trenches or wells in the island 105. The voids 260 may be created by any means known in the art.

As discussed above, one of the preferred actuation methods is electrostatics. This is accomplished by making the first actuator 220 on the compliant mechanism 100 and the second actuator 240 on the actuator frame 230 electrodes that are configured to receive command signals that, in turn, generate attractive electrostatic forces between the actuators 220 and 240.

Figure 3B:
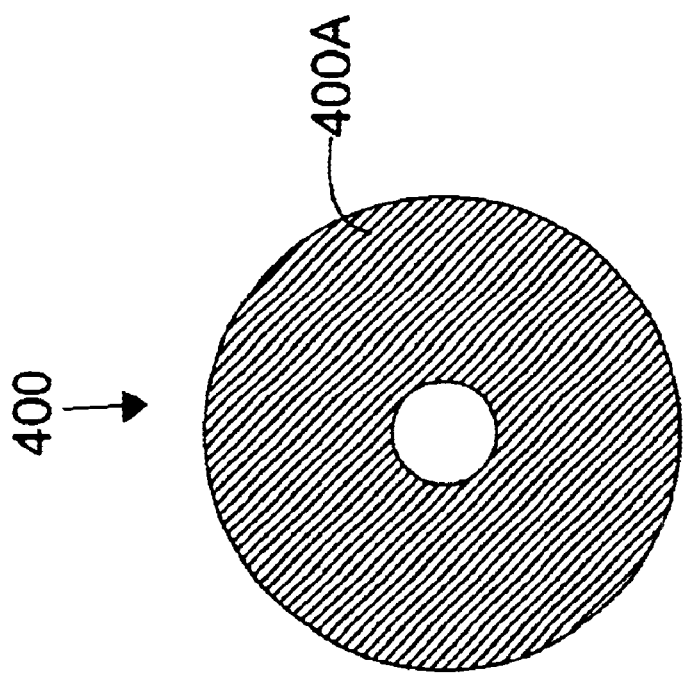
FIGS. 3A and 3B are plan views of a preferred embodiment of first and second sets of electrodes for implementing the first and second actuators, respectively, shown in FIG. 2.
Figure 3A:
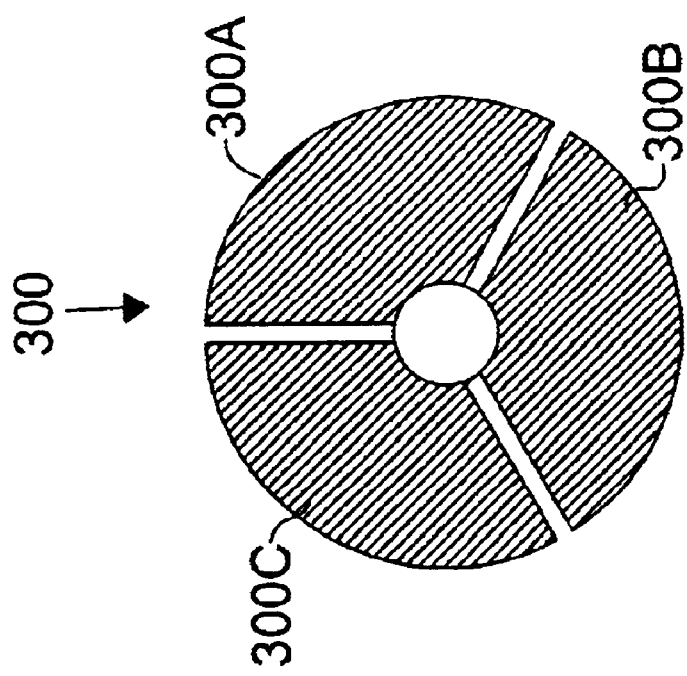

FIGS. 3A and 3B are plan views of a preferred embodiment of first and second sets of electrodes 300 and 400 for implementing first and second actuators 220 and 240, respectively. In this embodiment, three electrodes 300A–300C make up the first set of electrodes 300, and a single common electrode 400A is used for the second set of electrodes 400. It should be appreciated that this arrangement could be reversed, so that the three electrodes 300A–300C could be placed on the actuator frame 230, while the common electrode 400A is placed on the compliant member 110, underneath the island 105.

A particularly advantageous feature of certain preferred embodiments is to have three separately controlled actuator elements in the apparatus, each of which can be used to apply an independent force to a portion of the island 105. As shown in FIG. 3A, an optimal configuration is to employ three electrodes underneath the island 105. The voltage applied to each independent electrode generates an independent force, generally perpendicular to the surface of the island 105, centered at the geometric mid-point of the electrode segment. Each electrode segment has a distinct center of force. The electrode segments can be arranged such that these three centers of force are distributed advantageously across the surface of the island 105, enabling the actuators to actuate the island 105 to move into any desired position. The use of three centers of force provides for accurate, deterministic positioning for systems with three degrees of freedom.

As discussed above, first and second sets of electrodes 300 and 400 are configured to generate an electrostatic force when a command signal (voltage) is applied thereto. The command signal can be configured to create a repulsive or an attractive electrostatic force between the sets of electrodes 300 and 400. However an attractive electrostatic force is the preferred mode of operation.

During displacement, up and down motion of the island 105, and therefore the spacing of the gap between the first and second actuators 220 and 240, can be controlled by applying a voltage between the three electrodes 300A–300C and the counter-electrode 400A. The three-electrode structure shown in FIG. 3A for the first set of electrodes 300 allows for control of the tilt of the island 105, and therefore the optical component 420 mounted thereto, with respect to the frame 115. This is accomplished by selectively applying a stronger voltage to one or more of the three electrodes 300A–300C. Although, in this embodiment, three electrodes are used for the first set of electrodes 300, a different electrode pattern and a different number of electrodes can be used while still falling within the scope of the present invention.

In order to control tilt and gap spacing of the island 105, it is preferable to have a sensing mechanism that will indicate how much tilt and gap spacing is present. In one embodiment, the tilt and gap spacing is determined using optical feedback.

FIGS. 4A through 4E are cross-sectional views of steps in one preferred method of fabricating the compliant mechanism 100 of FIG. 1. It should be appreciated that, although FIGS. 4A–4E illustrate the fabrication of a single compliant mechanism 100, the fabrication process is designed so that a plurality of compliant mechanisms can be fabricated simultaneously on a single wafer. The method is preferably implemented with standard photolithographic processing techniques.

FIGS. 4A through 4E provide an example of a particularly advantageous feature of preferred embodiments of the invention. Embodiments of the present invention are particularly suitable for manufacturing in quantity by manufacturing multiple compliant mechanisms in parallel from a single wafer of material, such as silicon. Further, embodiments of the present invention provide for manufacturing each layer separate from the other layer and subsequently assembling the layers into multi-layer mechanisms. Such separate manufacture of each layer allows for materials and processing steps to differ substantially in each layer.

Figure 4A:
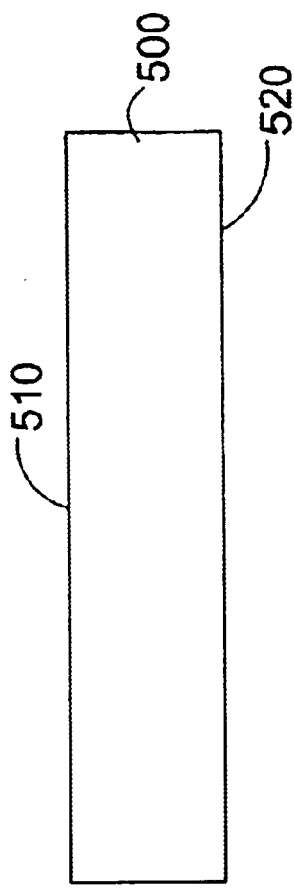
FIGS. 4A through 4E are cross-sectional views of steps in one preferred method of fabricating the compliant mechanism 100 of FIG. 1.

As shown in FIG. 4A, the fabrication method begins by providing a double-side polished silicon wafer 500, which is preferably approximately half a millimeter thick. As discussed above, although silicon is used in one preferred embodiment of the present invention, any of the materials known in the art that are compatible with microelectromechanical manufacturing techniques may be used. The silicon wafer 500 has a first side 510 and a second side 520. Both of these sides are preferably polished.

Figure 4B:
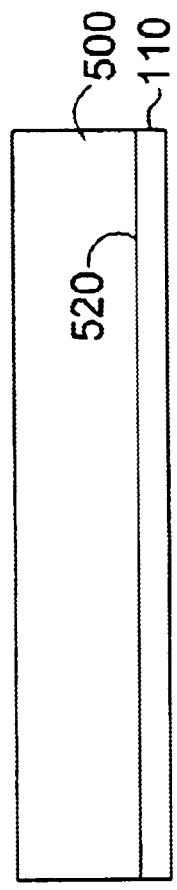
Figure 4C:
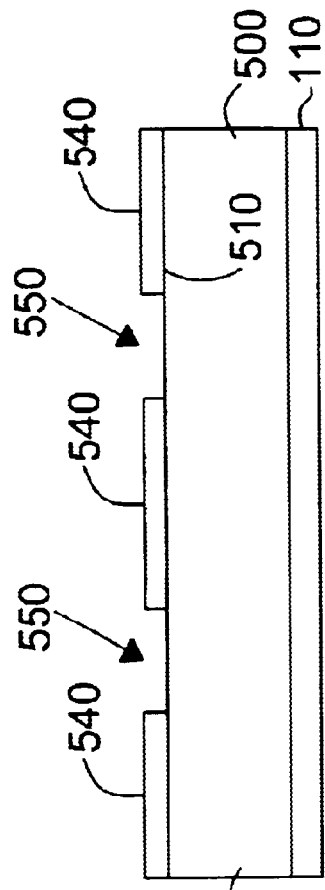

Next, as shown in FIG. 4B, the second side 520 of the silicon wafer is coated with a compliant material layer 530, preferably by spin coating to a desired thickness. Then, as shown in FIG. 4C, the first side 510 of the silicon wafer is coated with a photoresist layer 540, which is patterned to form an etch mask with openings 550 over the locations of the trench that will eventually be formed.

Figure 4D:
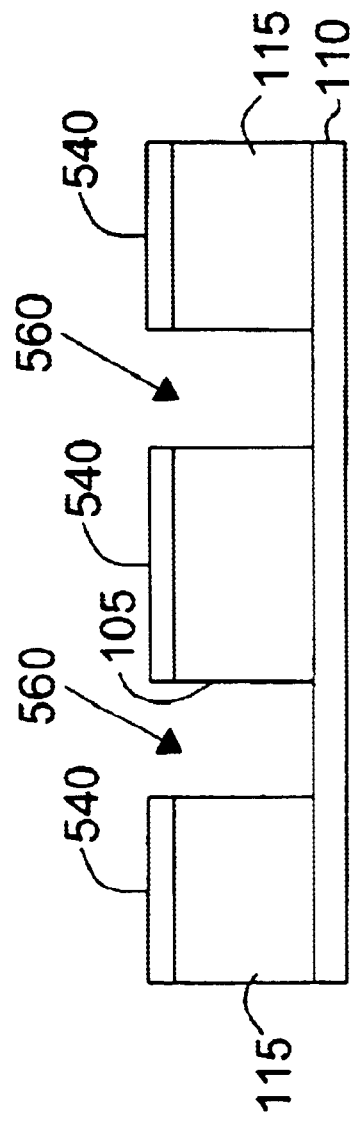
Figure 4E:
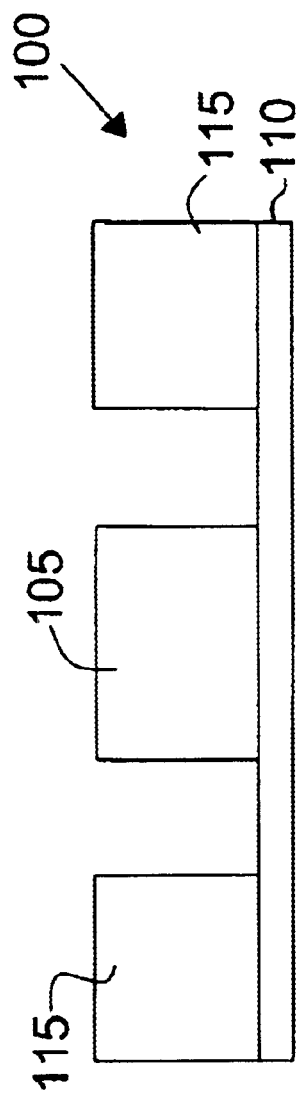

Then, as shown in FIG. 4D, a continuous trench 560 is etched down to the layer of compliant material 110, preferably using deep reactive ion etching (DRIE). The layer of compliant material 110 acts as an etch stop. The etching of the trench 560 forms the island 105 and the frame 115 of the compliant mechanism 100. Once the trench 560 is etched, the photoresist layer 540 is removed, as shown in FIG. 4E.

Although not shown, it should be appreciated that an optical component, or any other type of component, may be fabricated on the portion of the silicon wafer 500 that will eventually become the island 105, using any fabrication techniques known in the art, preferably prior to coating the silicon wafer 500 with the photoresist layer 540. Further, if the compliant mechanism 100 is to be used in an actuated device, such as the actuated device 200 shown in FIG. 2, electrodes may be fabricated on the compliant member 110, using any fabrication techniques known in the art.

It will be understood that persons of skill in the art might consider additional steps such as, for example, adding another layer between the compliant material and the silicon wafer 500.

In certain preferred embodiment the thickness of the compliant layer can be selected so that the thickness is approximately as large or larger than the width of the trench. This will enhance the longitudinal stiffness of the device by causing motion perpendicular to the island increasingly to generate sheer deformation in the compliant layer. This has advantages described in the co-pending applications.

In a preferred embodiment of a tunable filter, it is desirable not to have compliant material such as elastomer in the optical path of the device. This can be accomplished a number of ways, such as, for example, by exerzing the material after it is placed on the substrate in the regions where it is not desired. Alternatively, one can take advantage of the properties of materials as elastomer by curing the compliant materials only in the areas where it is desirable to have compliant material. Accordingly, after elastomer in spun on or otherwise applied, a mask or other technique can be used to avoid curing the region of the compliant material near the optical path. Effectively, this leaves an aperture through the elastomer.

Figure 5:
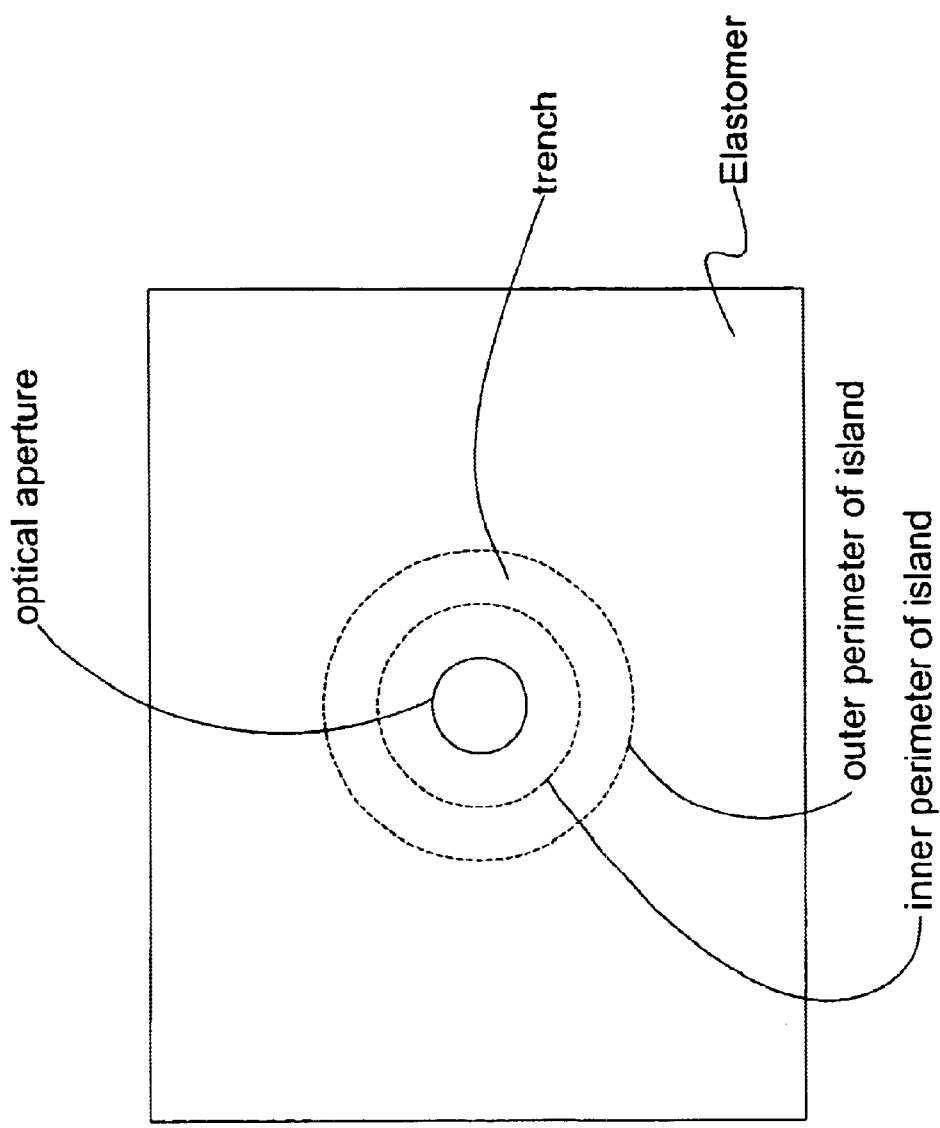
FIG. 5 is a plan view according to one embodiment.

As shown in FIG. 5, an optical apature is preferably formed on the elastomer. Under the elastomer, an outer perimeter of the island and an inner perimeter of the frame are shown. Between the inner and outer perimeters is the trench.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A movable compliant mechanism, comprising:
   a support member comprising a top and a bottom;
   an elastomer member attached to the bottom of the support member; and
   an island member movably supported by the elastomer member.

2. The apparatus of claim 1, wherein the support member comprises a frame.

3. The apparatus of claim 2, wherein the frame surrounds the island member.

4. The apparatus of claim 1, wherein the top of the island member is at least partially reflective.

5. The apparatus of claim 1, wherein the elastomer member has a Young's modulus that is smaller than a Young's modulus of the island member.

6. The apparatus of claim 1, wherein the elastomer member exhibits substantially linear-elastic behavior over an operational frequency range of the apparatus.

7. The apparatus of claim 1, wherein the island member and the support member comprise the same material.

8. The apparatus of claim 1, wherein the island member and the support member are fabricated from a common wafer.

9. The apparatus of claim 1, wherein a top surface of the island member is substantially level with the top of the support member when the island member is at a neutral position.

10. The apparatus of claim 1, wherein the island member and the support member are separated by a trench.

11. The apparatus of claim 10, wherein a thickness of the elastomer member is greater than or substantially equal to a width of the trench.

12. An actuated mechanism, comprising:
   a movable mechanism, comprising:
      a support member comprising a top and a bottom,
      an elastomer member attached to the bottom of the support member, and an island member movably supported by the elastomer member; and
      an actuator configured and positioned to move the island member in response to a control signal.

13. The actuated mechanism of claim 12, wherein the actuator comprises an electrostatic actuator.

14. The actuated mechanism of claim 12, wherein at least a portion of the actuator is attached to the island member.

15. The actuated mechanism of claim 12, wherein the actuator comprises:
   at least one electrode positioned on the elastomer member below the island member; and
   at least one electrode disposed on an actuator support.

16. The actuated mechanism of claim 15, wherein at least one of the electrodes comprises a three electrode structure.

17. The actuated mechanism of claim 12, wherein the island member and the support member comprise the same material.

18. The actuated mechanism of claim 12, wherein the island member and the support member are fabricated from a common wafer.

19. The actuated mechanism of claim 12, wherein a top surface of the island member is substantially level with the top of the support member when the island member is at a neutral position.

20. The actuated mechanism of claim 12, wherein the actuator is positioned exclusively on a side of the elastomer member opposite the island member.

21. The actuated mechanism of claim 12, wherein the island member comprises voids.

22. The actuated mechanism of claim 12, wherein the island member and the support member are separated by a trench.

23. The actuated mechanism of claim 22, wherein a thickness of the elastomer member is greater than or substantially equal to a width of the trench.

* * * * *